(12) United States Patent
Nordgren et al.

(10) Patent No.: US 11,317,894 B2
(45) Date of Patent: May 3, 2022

(54) SEALED CONTROL PANEL FOR MEDICAL EQUIPMENT

(71) Applicant: KONINKLIJKE PHILIPS N.V., Eindhoven (NL)

(72) Inventors: Timothy Fred Nordgren, Bothell, WA (US); Glenn Steven Arche, Bothell, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 387 days.

(21) Appl. No.: 16/310,914

(22) PCT Filed: Jun. 29, 2017

(86) PCT No.: PCT/EP2017/066215
§ 371 (c)(1),
(2) Date: Dec. 18, 2018

(87) PCT Pub. No.: WO2018/002272
PCT Pub. Date: Jan. 4, 2018

(65) Prior Publication Data
US 2019/0380683 A1    Dec. 19, 2019

Related U.S. Application Data

(60) Provisional application No. 62/356,654, filed on Jun. 30, 2016, provisional application No. 62/490,054, filed on Apr. 26, 2017.

(51) Int. Cl.
*A61B 8/00* (2006.01)
*G06F 3/0362* (2013.01)
*G06F 3/044* (2006.01)
*A61B 8/14* (2006.01)

(52) U.S. Cl.
CPC .............. *A61B 8/467* (2013.01); *A61B 8/14* (2013.01); *A61B 8/465* (2013.01); *A61B 8/54* (2013.01);
(Continued)

(58) Field of Classification Search
CPC ......... A61B 8/14; A61B 8/145; A61B 8/4405; A61B 8/4444; A61B 8/465; A61B 8/467;
(Continued)

(56) References Cited

U.S. PATENT DOCUMENTS 6,135,958 A    10/2000  Mikula-Curtis et al.
6,492,979 B1   12/2002  Kent et al.
(Continued)

FOREIGN PATENT DOCUMENTS

EP    2375314 A1 *  10/2011  ........... G06F 3/0418
EP    2375314 A1    12/2011
(Continued)

*Primary Examiner* — Boniface Ngathi N.

(57) ABSTRACT

A control panel may include a control surface and a plurality of user control areas at fixed locations along the control surface, a sealing layer extending continuously over the user control areas, wherein the sealing layer includes at least one topographical feature associated with at least one of the user control areas, and a pressure-sensitive capacitive touch layer provided at the at least one user control area, the a pressure-sensitive capacitive touch layer configured to detect a touch associated with an amount of pressure applied to the control surface at the at least one user control area and invoke a user control function associated with the at least one user control area responsive to the touch only if the amount of pressure exceeds a threshold amount.

16 Claims, 12 Drawing Sheets

(52) U.S. Cl.
CPC ............ *G06F 3/0362* (2013.01); *G06F 3/044* (2013.01); *A61B 8/145* (2013.01); *A61B 8/4405* (2013.01); *A61B 8/4444* (2013.01); *G06F 2203/04105* (2013.01)

(58) Field of Classification Search
CPC ......... A61B 8/54; G06F 3/044; G06F 3/0362; G06F 3/04886; G06F 2203/04105; G06F 2203/04809
See application file for complete search history.

(56) References Cited

U.S. PATENT DOCUMENTS

| | | | |
|---|---|---|---|
| 8,917,256 B2 | 12/2014 | Roziere | |
| 2006/0117275 A1* | 6/2006 | Jones | ...................... G06F 30/30 |
| | | | 712/201 |
| 2009/0085892 A1 | 4/2009 | Ishikura et al. | |
| 2010/0191120 A1 | 7/2010 | Kraus et al. | |
| 2013/0285735 A1* | 10/2013 | Snider | .................. H03K 17/962 |
| | | | 327/517 |
| 2014/0204699 A1 | 7/2014 | Dunkan et al. | |
| 2014/0437883 | 12/2014 | Cheng et al. | |
| 2015/0185885 A1 | 7/2015 | Lacroix | |
| 2015/0193056 A1 | 7/2015 | Bolender | |
| 2015/0199053 A1 | 7/2015 | Hotelling et al. | |
| 2015/0248165 A1 | 9/2015 | Ciesla | |

FOREIGN PATENT DOCUMENTS

| | | | |
|---|---|---|---|
| JP | 2014068819 A | 4/2014 | |
| WO | WO-2015136336 A1 * | 9/2015 | ............. A61B 8/467 |

\* cited by examiner

SEALED CONTROL PANEL FOR MEDICAL EQUIPMENT

This application is the U.S. National Phase application under 35 U.S.C. § 371 of International Application No. PCT/EP2017/066215, filed on Jun. 29, 2017, which claims the benefit of both Provisional Application Ser. No. 62/490,054, filed Apr. 26, 2017 and Provisional Application Ser. No. 62/356,654, filed Jun. 30, 2016. These applications are hereby incorporated by reference herein.

BACKGROUND

The present disclosure relates generally to operator control interfaces and more specifically to methods and apparatus for a sealed control panel for example for use with medical diagnostic equipment.

Control panels designed for use with medical diagnostic equipment (e.g., ultrasound systems) are generally designed so users can locate user controls by touch. This allows the user to focus on the image and the patient rather than on trying to locate buttons on the control panel. However, existing control panels with tactile controls may have certain shortcomings.

Also, current touch control panel such as those used for medical diagnostic equipment generally have a flat surface (e.g., a glass or plastic surface) which does not allow users to locate controls by touch. Further, these touch screen controls are invoked when they are touched, which does not allow an operator to first locate the control by sight and then rest a finger on the control without activating it until the appropriate time. Therefore, after an operator visually locates the control they must remain poised above it until they want to activate it. This situation can lead to repetitive stress injuries (RSI) and can also result in erroneous or premature control selections.

BRIEF SUMMARY

In accordance with one embodiment, a control panel may include a control surface, wherein a plurality of user control areas are arranged at fixed locations along the control surface. The control panel may further include a sealing layer extending continuously over the plurality of user control areas, wherein the sealing layer includes at least one topographical feature associated with at least one user control area of the plurality of user control areas. The control panel may further include a pressure-sensitive capacitive touch layer below the sealing layer and located at the least one user control area, wherein the pressure-sensitive capacitive touch layer is configured to detect a touch associated with an amount of pressure applied to the control surface at the least one user control area and invoke a user control function associated with at least one user control area responsive to the touch only if the amount of pressure exceeds a threshold amount.

In accordance with another embodiment, an ultrasound system may include an ultrasound imaging base configured to be coupled to an ultrasound probe and to control transmission of ultrasound and reception of ultrasound echoes with the probe and a control panel coupled to the ultrasound imaging base. The control panel may include a pressure-sensitive capacitive touch layer and a sealing layer disposed over the capacitive touch layer and comprising at least one topographical feature, wherein the at least one topographic feature is arranged at a location corresponding to an active portion of the pressure-sensitive, capacitive-touch layer, and wherein the active portion is configured to be activated responsive to application of an amount of pressure exceeding a threshold amount.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known devices, components, and user controls have not been shown in detail in order to avoid unnecessarily obscuring the described embodiments of the invention. Moreover, one or more aspects of the examples herein may not be shown to scale in the figures but may be exaggerated for purposes of illustration of the principles of the present invention.

Various embodiments will be described more fully hereinafter with reference to the accompanying drawings. In explanations of the various embodiments, the same or corresponding elements may be denoted by the same reference designators. For the sake of brevity and to avoid duplicate explanation, descriptions to the same elements as set forth in one embodiment may be omitted or only briefly mentioned in each succeeding embodiment.

Figure 1:
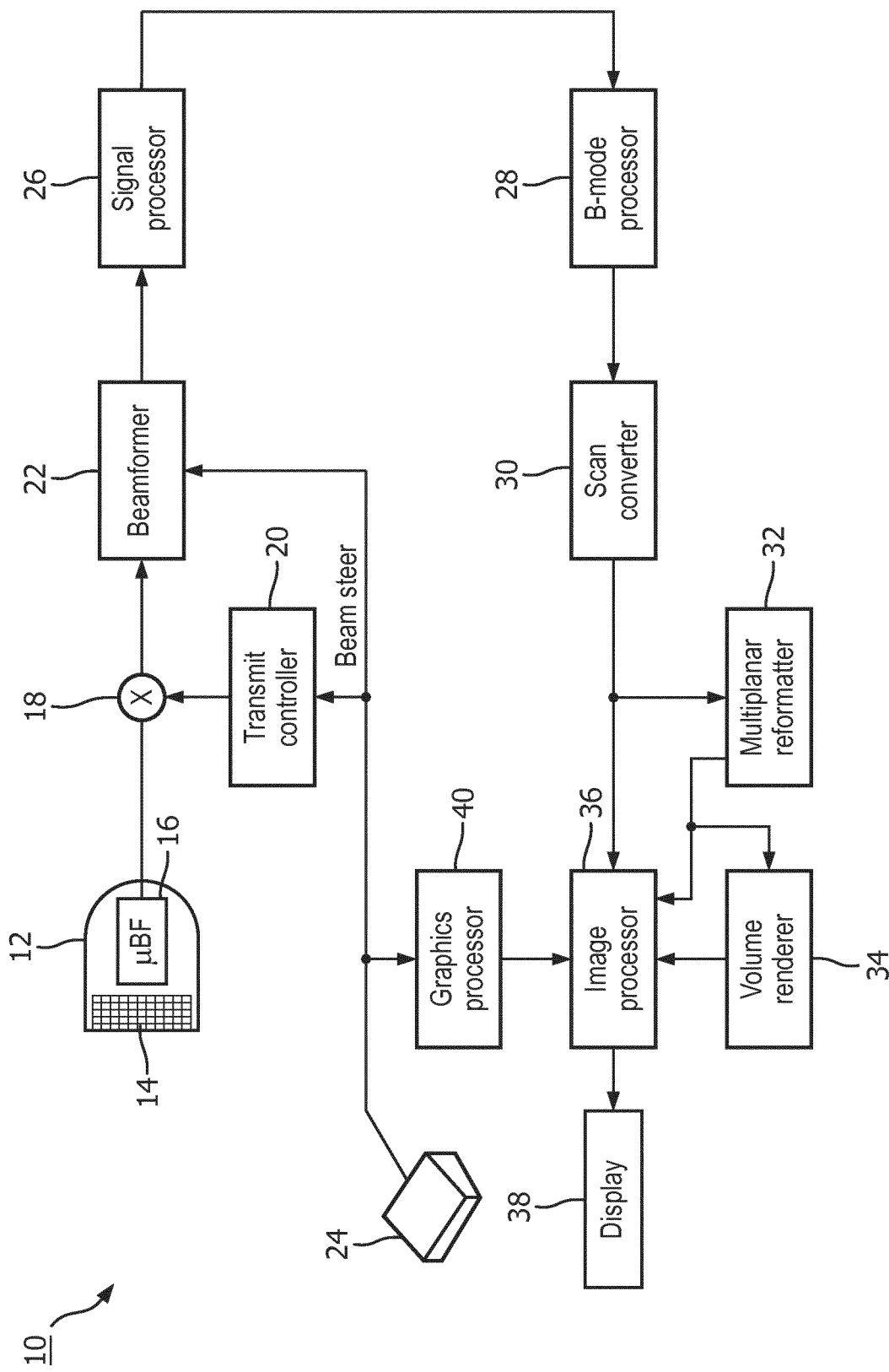
FIG. 1 is a block diagram of an ultrasound imaging system constructed in accordance with the principles of the present invention.

Referring to FIG. 1, an ultrasound imaging system 10 constructed in accordance with the principles of the present invention is shown in block diagram form. In the ultrasonic diagnostic imaging system of FIG. 1, an ultrasound probe 12 includes a transducer array 14 for transmitting ultrasonic waves and receiving echo information. A variety of transducer arrays are well known in the art, e.g., linear arrays, convex arrays or phased arrays. The transducer array 14, for example, can include a two dimensional array (as shown) of transducer elements capable of scanning in both elevation and azimuth dimensions for 2D and/or 3D imaging. The transducer array 14 is coupled to a microbeamformer 16 in the probe 12 which controls transmission and reception of signals by the transducer elements in the array. In this example, the microbeamformer is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 36 can generate graphic overlays for display with the ultrasound images. These graphic overlays can contain, e.g., standard identifying information such as patient name, date and time of the image, imaging parameters, and the like. For these purposes the graphics processor receives input from the control panel 24, such as a typed patient name. The control panel can also be coupled to the multiplanar reformatter 32 for selection and control of a display of multiple multiplanar reformatted (MPR) images.

Figure 2:
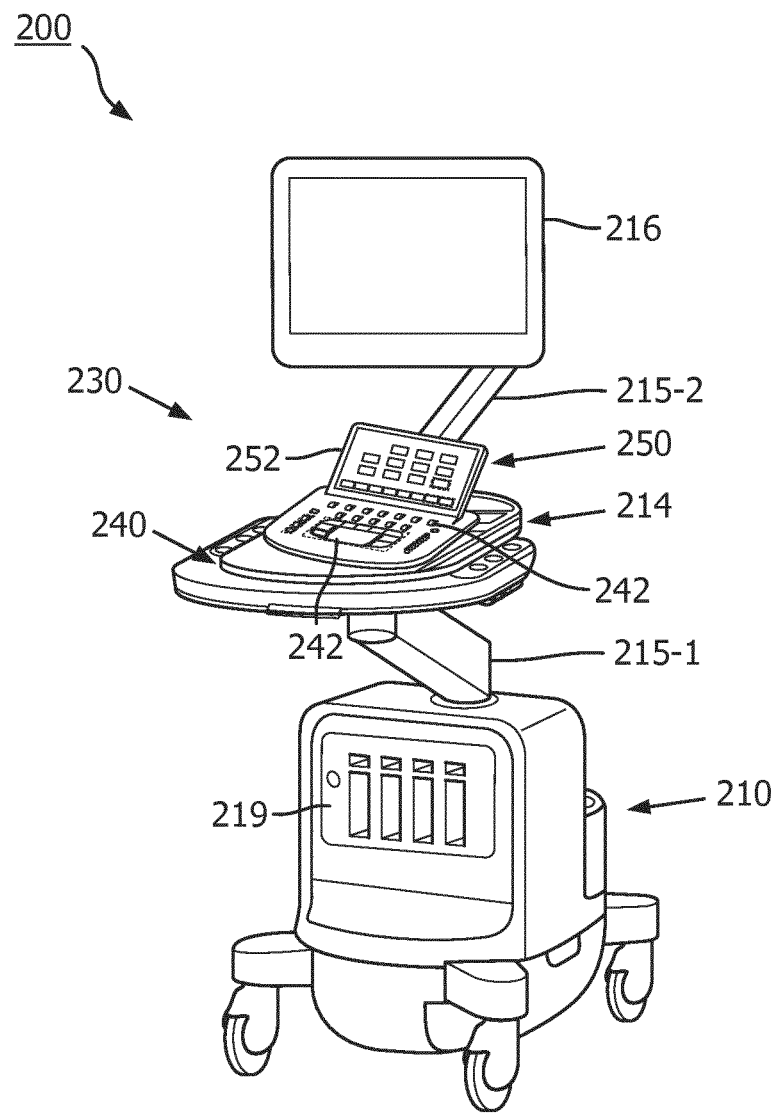
FIG. 2 is an illustration of an ultrasound imaging system which may include a control panel in accordance with the principles of the present invention

FIG. 2 shows an illustration of an ultrasound imaging system which may include a control panel in accordance with principles of the present invention. The ultrasound imaging system 200 may include one or more of the components of the ultrasound imaging system 10 previously described. For example, the ultrasound imaging system 200 may include beamformer, signal processor, B-mode processor, scan converter, multiplanar reformatter, volume renderer, image processor, graphics processor, and/or other processors which may control various operations of the ultrasound imaging system. One or more of these components may be provided in an ultrasound imaging base 210. In some examples, the ultrasound imaging base is implemented in the form of a mobile base or cart 219 (e.g., as shown in FIG. 2). In other examples, one or more of the components of the ultrasound imaging system may be implemented in hardware and software and provided in a portable form (e.g., a tablet computer). In other words, the ultrasound imaging base may be implemented in the form of a portable computer (not shown).

The ultrasound imaging base may be configured to be coupled to an ultrasound probe (e.g., probe 12 of FIG. 1) and to control transmission of ultrasound and reception of ultrasound echoes with the probe. The ultrasound imaging system 200 may include a one or more components which provide a user interface 230 for controlling the operation of the system. The user interface 230 may include a display 206, e.g., for displaying image data. In the illustrated embodiment, the display 206 is attached to the cart 219 via an articulating arm 215-2 which enables re-positioning of the display 206 such as to allow a displayed image to be viewable by others (e.g., the patient, another ultrasound operator, or a clinician).

The user interface 230 may include one or more user controls, which may be provided on a control panel 214, which may also be coupled to the base 219 via an articulating arm 215-1. In some examples, the user controls may include hard controls (e.g., mechanical controls) and soft controls (e.g., graphical user interface elements). By hard controls, it is generally implied that a position and/or control functions of a particular control may be fixed (e.g., hardwired), while typically soft controls refer to user controls which may be re-configurable (e.g., to change a location of the control and/or functionality of the control). One or more of the controls 242 may be arranged on a field panel 240. The field panel may be generally horizontal (plus or minus 25 degrees) which may correspond to a preferred ergonomic position. One or more of the controls 242 may provide a tactile interface whereby a user may locate certain controls by touch. Alternatively or additionally, one or more soft controls may be provided in a display area 252 of a touch-sensitive display 250.

Flat control panels such as those provided by touch-sensitive displays have the advantage of configurability (e.g., different user controls may be provided in different user interface screens for virtually any number of different applications). However, one drawback of existing flat control panels is the inability for a user to locate controls by touch. Thus, to locate a particular control, a user may need to turn their attention to the touch screen and away from the patient or image to locate the control. Also, once located, invocation of functions associated with soft controls on existing touch control panels may be instantaneous regardless of the force applied to the soft control. As such, the user may need to "hover" their finger over the soft control until ready to invoke the function. That is, after a user visually locates a control their finger must remain poised above the control until they are ready to select the control. This scenario may not be idea as it may cause repetitive stress injuries (RSI). In the interim, the operator may be making adjustments such as moving the probe to better align it for imaging a target which may result in the user's finger having drifted from the control's location, which may further cause false control selections. To avoid it, the user may need to return their focus to the touch panel just prior to selecting the desired control, thus creating further workflow inefficiencies. Control panels in accordance with some of the examples herein may address some these problems.

Conventional ultrasound imaging systems often include tactile controls (e.g., mechanical controls such as push buttons, knobs, switches and the like, which allow an operator to locate controls by touch without having to divert their attention from the image or patient. However, while mechanical controls may provide such a tactile interface, the use of mechanical controls may have drawbacks particularly in medical application where cleaning and sterilization of medical equipment including the control panels of ultrasound systems is necessary. To minimize bioburden build-up a control panel of a medical imaging system may need to withstand high levels of liquid disinfectants. Generally, mechanical controls introduce openings or gaps in a control surface, which may increase the risk of damage to the control panel, e.g., due to liquid intrusion into the panel. According to the examples herein, an improved control panel for a medical imaging system, such as ultrasound system, may be provided. While examples are described in the context of an ultrasound imaging system, it will be understood that control panels in accordance with the present disclosure may be provided for any other type of medical imaging system, or more broadly other medical equipment that includes a control panel. The examples herein may also be used in other applications such as in industrial applications (e.g., control panels of manufacturing machines or vehicles where contamination from oil, chemicals, or debris may be a concern) or consumer applications (e.g., control panels of consumer products such as TV, video games, home appliances, etc.) and other applications.

Figure 3:
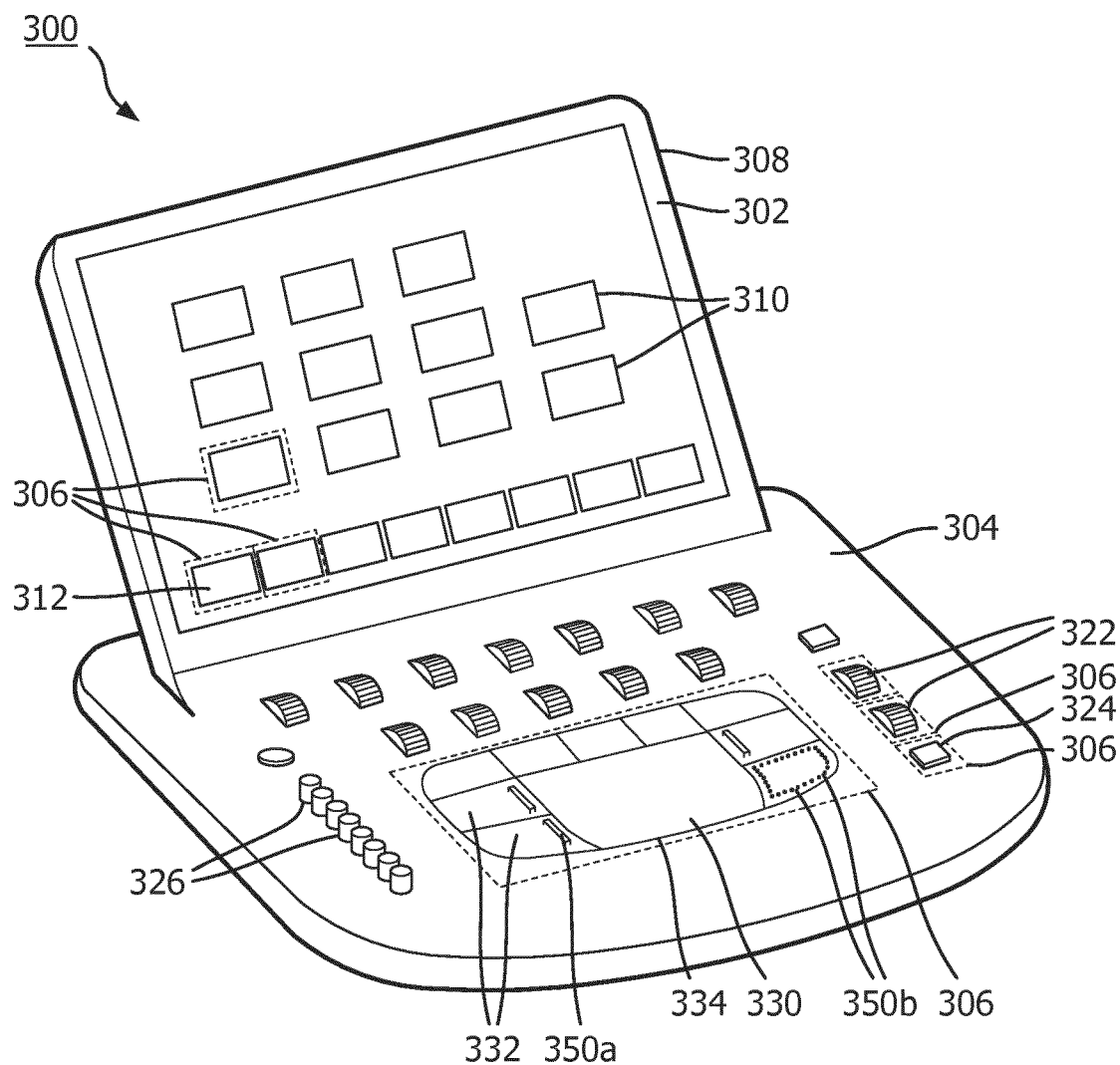
FIG. 3 is a perspective illustration of an embodiment of a control panel in accordance with the principles of the present invention.

FIG. 3 is a perspective drawing a control panel in accordance with the present invention. The control panel 300 may be used to implement the control panel 214 of FIG. 2. The control panel 300 may include one or more control surfaces (e.g., an upper surface or panel 302, a lower surface or panel 304, or both as shown in the example in FIG. 2). In other examples, the control panel 300 may include only a single control surface or panel. In some examples, the control panel 300 may include a touch sensitive display panel for the lower panel 302.

The control panel 300 may include a plurality of user control areas (e.g., control areas 306) provided at fixed locations along a control surface of the control panel 300. The control areas may correspond to user controls of the control panel 300. A sealing layer (e.g., sealing layer 316) may extend continuously over one or more of the user control areas. In some examples, the sealing layer 316 may extend continuously over all of the user control areas of a given control surface. The sealing layer 314 may include at least one topographical feature (e.g., topographical feature 316) which may be associated with at least one of the user control area. A pressure-sensitive capacitive touch layer (not shown in the view FIG. 3) may be provided below the sealing layer 306 at least one of the user control areas. The capacitive touch layer may be a single continuous encompassing a plurality and in some cases all of the user control areas of the control panel. In other examples, a plurality of separate or discrete capacitive touch sensors may form the capacitive touch layer. The pressure-sensitive capacitive touch layer may be configured to activate a user control responsive to a touch, which is associated with an amount of pressure exceeding a threshold amount. For example, the pressure-sensitive capacitive touch layer may be configured to detect a touch which is associated with an amount of pressure applied to a given user control area and to invoke a function of the user control area responsive to the touch only if the amount of pressure exceeds a threshold amount.

In some examples, the sealing layer may be opaque and may be colored or patterned (e.g., via an in-mold labeling process) with graphics such as to indicate the type of control or provide information about the control or its operation. In some examples, the sealing layer may be partially transparent such as to allow illumination of graphics that may be patterned on the sealing layer. In further examples, the sealing layer may be translucent, so as to allow diffused illumination from below such as to indicate active controls. Illumination may be provided via a light source such as an LED or other type of backlighting located below the sealing layer. In yet further examples, the sealing layer may be substantially optically transparent, such as when used in combination with a touch sensitive display, to allow displayed graphics to be visible though the sealing layer, an example of which is described further below.

The upper panel 302 may include a display 308. The display 308 may be implemented using liquid crystal display (LCD) technology, light-emitting diode (LED) display technology, organic light-emitting diode (OLED) display technology or another type of display technology. The display 308 may be configured to detect a touch such as made by a finger or stylus at one or more locations on the display 308, and may also be referred to as touch-sensitive display or touch screen. The display 308 may be configured to provide one or more soft controls, for example by displaying a graphical representation of a user control such as a button (e.g., a GUI control element) over a designated area on the touch-sensitive display 308. The soft controls may include variable-location soft controls 310 and fixed-location soft controls 312. Variable-location soft controls 310 may be provided at different locations on the display 306, such as when displaying different user interface screens which may have different layouts of the various user interface elements. A fixed-location soft control 312 may be displayed in a fixed location, such as in a row along the bottom of the display 306. While the functionality of both the variable-location and fixed-location soft controls may vary depending on the particular user interface screen being displayed, the fixed-location soft controls associated with a particular user interface screen may always be provided in a specific location and arrangement on the display 306.

The lower panel 304 may include any number of user controls (e.g., faux rotary encoders, pushbuttons, or sliders 322-326, respectively, a trackpad 330, and control buttons 332, or others) which may resemble mechanical operator controls of different types. The user controls may be made to resemble real mechanical controls such as to provide a tactile interface. The user controls may be made to resemble real mechanical controls via a combination of topographical features 334 and/or shaping of the sealing layer and any support layers that may be incorporated in a given configuration of a control panel in accordance with examples herein.

Faux rotary encoders 322 may be designed to resemble and mimic the function of a real (e.g., electro-mechanical) rotary encoder. A faux rotary encoder may be configured to receive user input in the form of a finger swipe to mimic the rotary movement of a real encoder, rather than requiring an actual rotary input. As such, a faux rotary encoder may be provided below a continuous sealing layer facilitating a sealed control panel that does not include openings as may otherwise be required to accommodate a rotary shaft. A faux rotary encoder may be implemented using a touch-sensor (e.g., a capacitive sensor) which is operable to detect a finger swipe. Additionally to the touch-sensor, topography may be imparted to provide a tactile feel of the faux rotary encoder 322 such as to enable locating of the control by touch. Given a sealed protrusion formed to feel like a knob where multi-touch projected capacitance could sense a grasp with multiple fingers (thumb, index, and middle finger) and a turning movement as an encoder count up or down. Tactile and/or audible feedback may be utilized to provide user feedback along with that given on an imaging display or touch panel display.

Faux sliders 326 may be designed to resemble and mimic the function of any of a variety of slider controls, such as a TGC (Time Gain Compensation) slider used on some ultrasound machines. As shown in FIG. 3, multiple knob-like protrusions can be included in the control panel in order to look like TGC slider knobs. A faux slider 326 may be configured to sense the application of a touch, or touch with pressure along a side of the control to mimic the sliding motion of a real (e.g., electro-mechanical) slider without necessitating actual movement of the faux slider. For example, pushing on one side or the other of the knobs with fingers (or a hand) could be sensed by the knob via projected capacitance or a force sensor and be distinguished as an increase or a decrease of time gain compensation (TGC). A tap on the top, or a touch on both sides could "center" the gain. Tactile and/or audible feedback may be utilized to provide user feedback along with that given on an imaging display or touch panel display. As such, a faux slider may be implemented below a continuous sealing layer to enable a sealed control panel that does not include openings such as may otherwise be required to accommodate the input shaft of a real slider. Faux pushbuttons 324 and control buttons 332 may function similar to mechanical pushbuttons, where downward pressure would activate or toggle the corresponding function, but without necessitating actual downward displacement of the upper surface of the user control. Trackpad 330 may function similar to a traditional trackpad, with taps representing "clicks" or activating actions and finger swipes representing movement of a cursor or item. Trackpad 330 may provide the functionality of a trackball without the need for the rotating component of a conventional trackball.

Secondary topographical features or surface features may be provided on or near some of the user controls, for example in the form of raised bars or surfaces 350a, bumps 350b, which may outline or provide a locator for a specific control, or any other type of topographical features including but not limited to depressions, holes, raised bars, plateaus, bumps, ridges, and surface textures, or combinations thereof, may be used for example to aid in locating a specific control by touch.

One advantage of using faux controls such as the faux encoders 322 and faux sliders 326, examples of which will be described further with reference to FIGS. 7 and 8, may be to enable a top surface of the control panel 300 to be provided as a single continuous layer (e.g., a sheet of material) which may seal the underlying components of the control panel 300 from the external environment. This may prevent or reduce the risk of ingress of contaminants and bioburden and may thereby protect sensitive electronics for example from liquid disinfectants and other materials.

Figure 4:
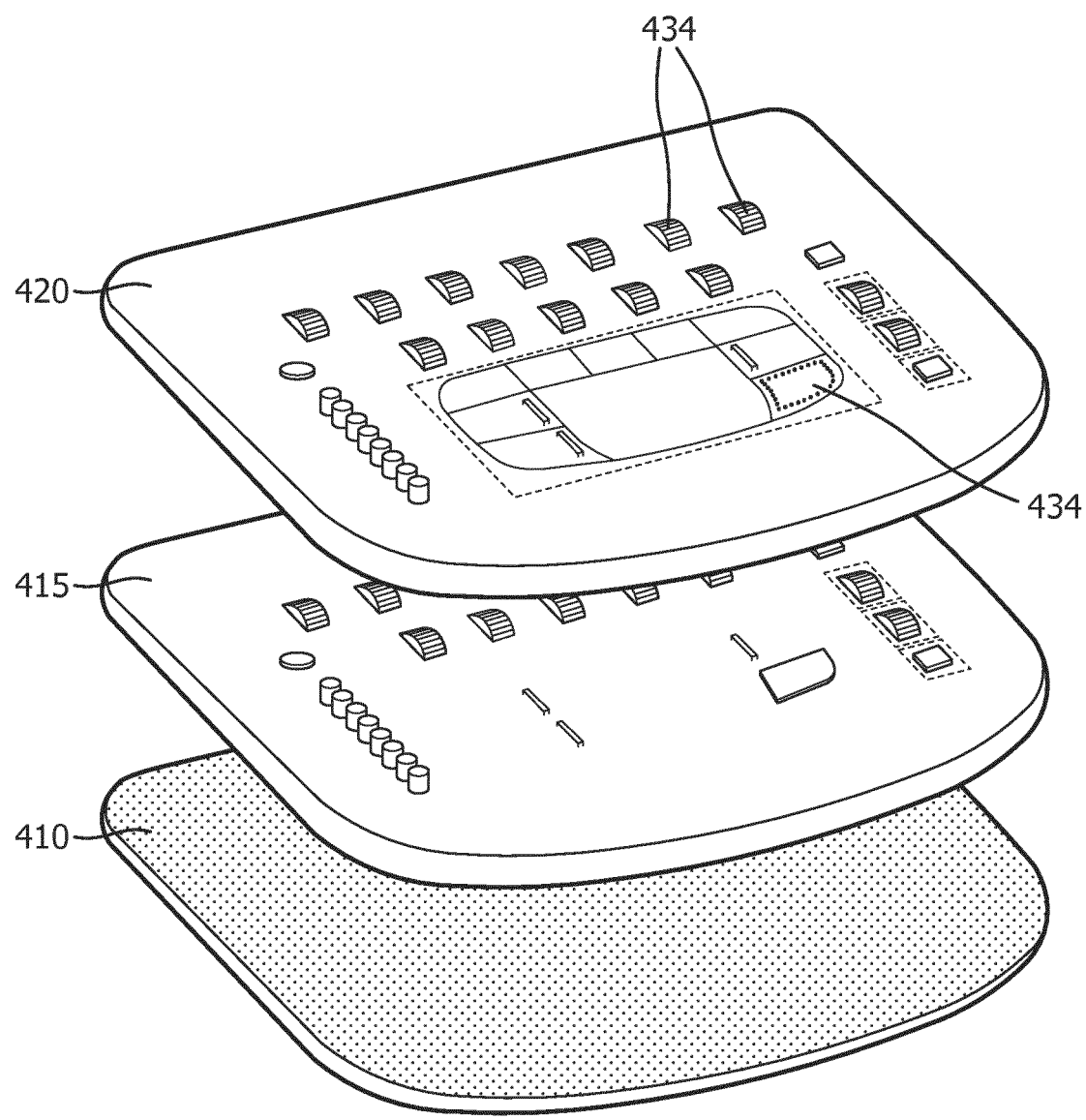
FIG. 4 is an exploded, perspective illustration of an embodiment of a control panel in accordance with the principles of the present invention.

FIG. 4 is an exploded, perspective view of an embodiment of a control panel 400, showing exemplary layers of a control panel in accordance with the present disclosure. The control panel 400 may be used to implement the lower panel 204 of FIG. 3.

The top-most, outer layer of the control panel 400 is a sealing layer 420 which may be implemented as a single, seamless piece of material. The sealing layer 420 may be constructed from a pressure-formed (e.g., vacuum-formed) film. The sealing layer 420 may be shaped, for example using a pressure-forming process, from a generally flat sheet of material to a shaped layer which includes any number of topographical features 434. In some examples, the sealing layer 420 may be provided with additional features (e.g., labels, coloring, etc.) for example using any of a number of known processes, including but not limited to an in-mold-decoration (IMD) process, an in-mold-label (IML) process. The material used for the sealing layer 420 may be a plastic film, such as polyester, of polyethylene terephthalate (PET) or another type of plastic material, which may be silk-screened to included decorations, labels, colors, and the like.

The sealing layer 420 may be designed such that it has no holes. In some examples, the sealing layer 420 may be shaped such that the end portions of the sealing layer are bent or shaped down to extend over an edge of the control panel. This may create a sealing lip against a back enclosure (not shown) to protect electronics and other layers of the control panel. As the sealing layer 420 may be designed to have no openings or holes, the controls typical of a standard control panel, which may include rotary encoders and slider controls with moving parts necessitating an opening in the layer, these controls may be replaced with the faux encoders 322 and faux sliders 326 described with reference to FIG. 3.

Below the sealing layer 420 is a capacitive touch layer 410. The capacitive touch layer 410 is sensitive to and detects the capacitance present in a finger or another object (e.g., a stylus) brought near or in contact with the capacitance touch layer 210. The sensitivity of the capacitive touch layer 410 may be tuned for example by tuning control parameters of a controller, such as an AMTEL touchscreen controller. In some embodiments, the capacitive touch layer 410 is a projected capacitance, or P-Cap, layer. In other examples, other types of capacitive touch technology may be used. The capacitive touch layer 410 is configured to be pressure-sensitive. For example, the capacitive touch layer 410 may be coupled to a controller to be able to detect an amount of pressure or force associated with touch, thereby allowing different functions to be enabled based on the amount of pressure of the detected touch. The capacitive touch layer 410 may be coupled to a controller, which may be positioned elsewhere within an enclosure of the system, e.g., a flexible circuit (not shown). In one embodiment, the capacitive touch layer 410 may be configured to perform a function (e.g., invoke the functionality of a user control associated with a particular user control area to which pressure is applied) only if the pressure exceeds a threshold. In this manner, the capacitive touch layer 410 may enable an operator to tactilely locate and to rest a finger on a control lightly without activating the control, and only activate the control when additional pressure exceeding the threshold is detected by the capacitive touch layer 410. The pressure threshold may be tuned as appropriate for a particular application and/or taking into consideration the specific panel configuration (e.g., number of layers, thickness of layers, type of user control, etc.)

In some examples, option one or more support layers may be provided between the sealing layer 420 and the capacitive touch layer 410 (e.g., support layer 415 as shown in FIG. 4), below the capacitive touch layer, or both. The support layer 415 may provide a support structure for the relatively thin sealing layer. The support layer 415 may follow a contour of the shaped sealing layer such as to fill in cavities defined between by the contour of the sealing layer 420. The support layer 415 may be created by backfilling the "shell" of the sealing layer 420 with an injection molding process.

Additional examples of layers that may be used in the construction of a control panel according to the present disclosure are described with reference to FIGS. 3A-3D. FIGS. 3A-3D.

Figure 5A:
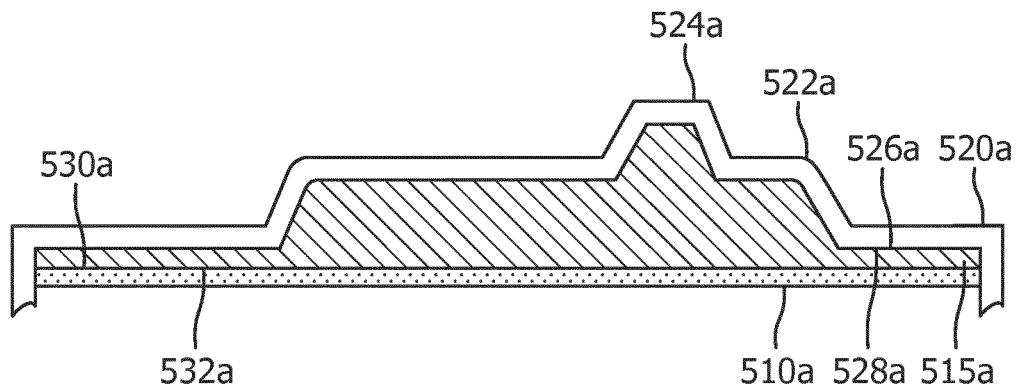
FIGS. 5A-5C are cross-sectional illustration of exemplary layered structures for control panels in accordance with principles of the present invention.
Figure 5B:
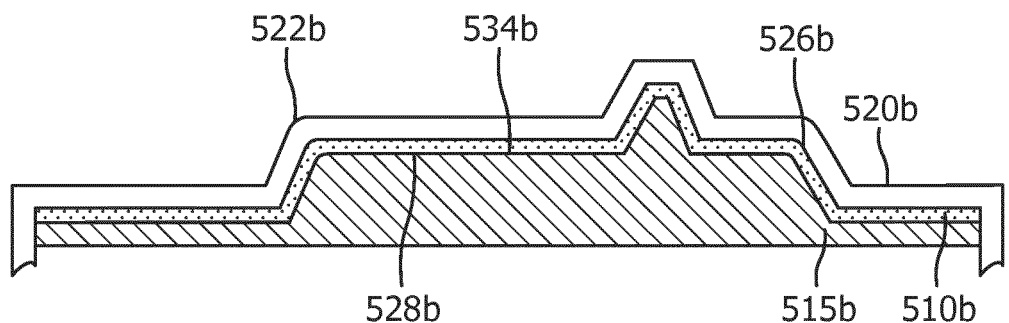

FIG. 5A shows a cross-sectional view of layers of a control panel in accordance with one embodiment. A sealing layer 520a is provided as the upper-most or top layer and encloses underlying layers and/or electronics of the control panel. The sealing layer 520a may extend continuously over a plurality of user control areas of the control panel. The sealing layer 520a may thus provide an environmental seal. The sealing layer 520a may include topographical features 522a and 524a, which may aid an operator in locating a user control area by touch. The sealing layer 520a may have a lip around its outer edge that extends down and over the outer edges of the other layers and to provide a seal against contaminants. Some of the topographical features (e.g., feature 522a) may be shaped such that the particular location along the sealing layer resembles a mechanical control. For example, the sealing layer 520a may be shaped (e.g., via pressure forming) to include a topographical feature in the form of a protrusion that resembles a mechanical control, such as a push button or other type of control. Some of the topographical features (e.g., feature 524a) may be secondary features that are associated with another topographical feature (e.g., feature 522a). The secondary topographical feature may provide additional locator functionality to enable to the user to locate a specific one of a plurality of similarly shaped controls.

Below the sealing layer 520a is a support layer 515a, which is shaped to mirror a contour of the sealing layer 520a. In other word, an upper surface 528a of the support layer may have the same shape as the lower surface 526a of the sealing layer 520a. As described, the sealing layer may be a shaped film pressure formed to follow a predetermined contour and the support layer may be a molded plastic layer that fills the cavities defined by the shape of the sealing layer 520a. The sealing layer 520a may be relatively thin (e.g., up to 1 mm, up to 5 mm, or greater) thus the support layer 515a may provide structural support for the topographical features 522a, 524a formed in the sealing layer 520a and/or for the sealing layer 520a itself. In some examples, the secondary topographical features 524a may be substantially smaller than other topographical features and may not have a corresponding contoured lower surface but may be formed as projections from or indentations on the upper surface of the sealing layer 520a. The bottom surface 530a of the support layer 515a may be generally flat and correspond to the planar surface of the capacitive touch layer 510a.

Below the support layer 515a is a capacitive touch layer 510a. In this example, the capacitive touch layer 510a is a generally planar layer that provides a touch sensing function for the control panel. As described, the capacitive touch layer 510a may be a p-cap layer and in preferred examples a pressure-sensitive p-cap layer. In operation, a finger or stylus would come in contact with the upper surface of the sealing layer 520a. Varying amounts of pressure associated with a touch by a finger or stylus on the sealing layer 520a may be detected by the capacitive touch layer 510a through the support layer 515a. In one embodiment, the capacitive touch layer 510a may be a pressure-sensitive P-Cap layer which is configured to cause functionality of a user control to be invoked only if the pressure exceeds a predetermined amount. In some examples, the amount of pressure may be determined based on the size of the touch "footprint" detected on the sealing layer 520a. For example, a light touch on the sealing layer 520a may detected as a small circle representing only the small point of contact by the finger makes with the sealing layer 520a, and a heavier touch (more downward pressure) may be detected as a circle of a larger diameter (e.g., as the tip of the finger spreads out on the sealing layer 520a from the increased pressure.

Although the example above describes the use of a pressure-sensitive P-Cap technology, any appropriate capacitive touch technology may be used.

FIG. 3B shows another embodiment for the layered structure of a control panel in accordance with the examples herein. In this embodiment, the layers again include an upper-most or top sealing layer 520b, a support layer 515b, and a capacitive touch layer 510b. The support layer 515b is provided below the capacitive touch layer 510b such that the capacitive touch layer 510b is sandwiched between the sealing layer 520b and the support layer 515b. In this embodiment, the capacitive touch layer 510b is a shaped layer, the contour of may follow the contour of the sealing layer 520b. The capacitive touch layer 510b may be flexible (e.g., implemented using flexible circuitry) and may be configured to fit in the cavities defined by the sealing layer 520b by the support layer 515b. In other words, the lower surface 526b of the sealing layer 520b may correspond in shape to the upper surface 532b of the capacitive touch layer 510b. The support layer 515b has a contoured upper surface 528b which corresponds in shape to the lower surface 534b of the capacitive touch layer 510b to thereby provide support for the two shaped layers above. In this example, the layers structure may include one or more topographical features 522b and 524b which may be similar to those in the previous example.

FIG. 3C shows another embodiment of a layer structure for a control panel in accordance with the examples herein. In this embodiment, the capacitive touch layer 510c is a planar layer and the sealing layer 520c is provided directly over the capacitive touch layer 510c. The lower surface 526c of the sealing layer 520c corresponds to the upper planar surface 532c of the capacitive touch layer 510c. The layered structure may be formed by molding the sealing layer 520c and support layer 515c together, such as through an injection molding or overmolding process. Thus, in some examples, the two layers may be formed as one piece 220a. In other examples, the sealing layer 520c and capacitive touch layer 510c may be formed separately and then bonded together.

Figure 6A:
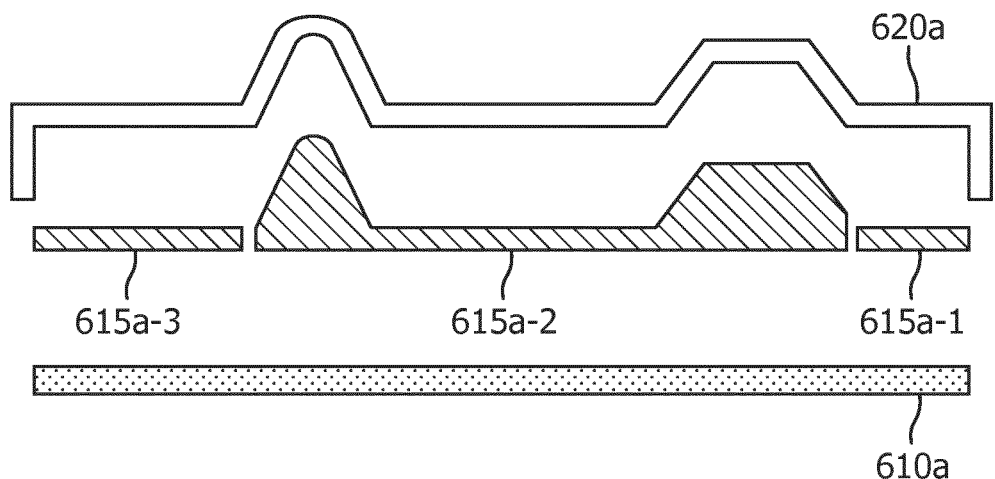
FIGS. 6A-6B are cross-sectional illustration of further examples of layered structures for control panels in accordance with principles of the present invention.
Figure 6B:
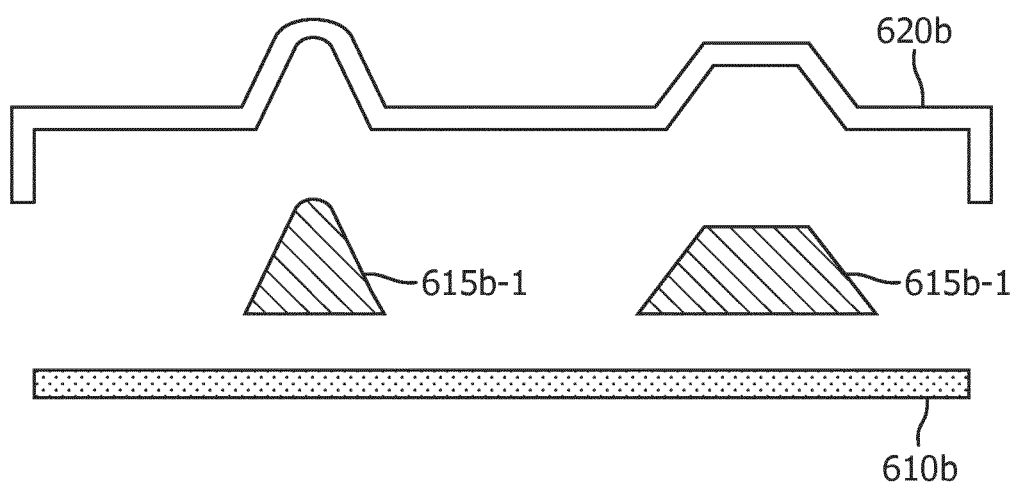

FIGS. 6A and 6B show further embodiments of layer structures for control panels in accordance with the present disclosure. In the examples in FIGS. 6A and 6B, the layered structure similarly includes a capacitive touch layer 610a and a sealing layer 620a with the support layer being discontinuous. In the embodiment in FIG. 6A, the support layer is formed of a plurality of separate support pieces 615a-1-615a-3, which may abut one another in the assembled control panel, or may be slightly spaced apart. In the illustrated example, only three separate support pieces are shown, however, any appropriate number of support layer pieces may be used in other examples.

Separating the support layer into components (such as support pieces 615a-1, 615a-2, and 615a-3) may improve touch detection such as by isolating one user control from another. A touch (e.g., by a finger) on the sealing layer 620a directly above the support layer piece 615a-2 may be less likely to cause detection of a touch at the adjacent support layer pieces 615a-1 or 615a-3. A discontinuous support layer may be formed, for example by an insert molding process in which inserts are provided at the locations of separation during the molding of the support layer. In other examples, the support pieces may be formed as separate components that are then assembled (e.g., bonded) to the other layers.

In the embodiment in FIG. 6B, the support layer is again a discontinuous layer, but in this example, the support layer is provided only within the cavities defined by the lower surface of the sealing layer 620b. In this example, a portion of the lower surface of the sealing layer 620b is provided in contact with the capacitive touch layer 610b and support pieces (e.g., 615b-1 and 615b-2) fill only the space between the sealing layer 620b and capacitive touch layer 610b, such as may be formed due to the inclusion of topographical features in the sealing layer 620b. In this embodiment, an additional support layer (not shown) may be provided below the illustrated layered structure, to provide additional support to the sealing layer 620b and capacitive touch layer 610b.

Figure 7A:
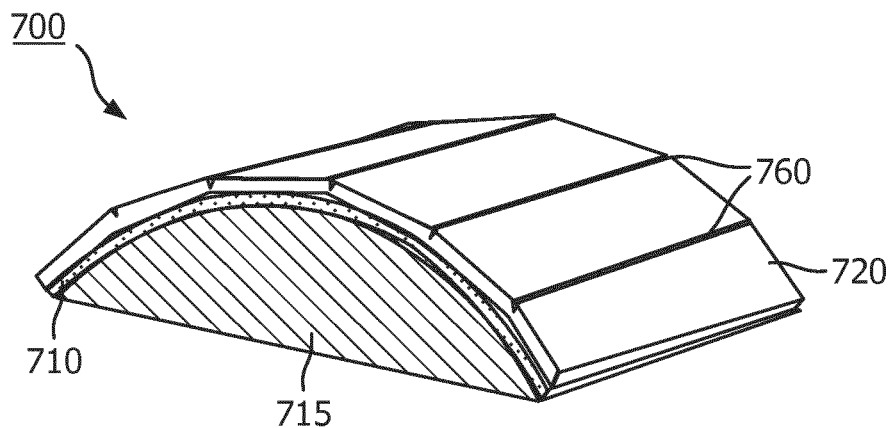
FIGS. 7A and 7B are perspective and exploded illustrations of a faux encoder for a control panel in accordance with the present disclosure.
Figure 7B:
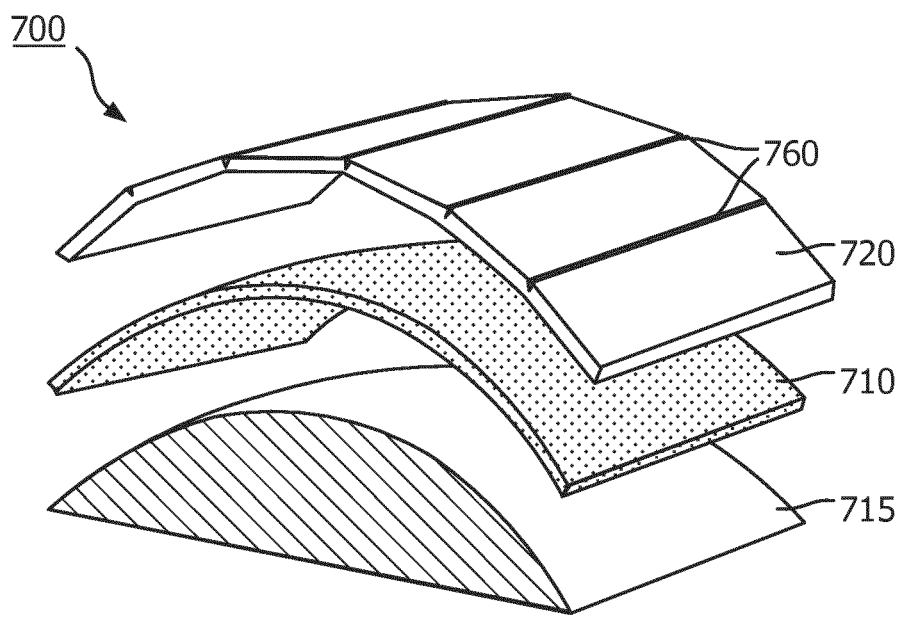

FIGS. 7A-7B are perspective drawings of an example user control in accordance with further examples. The user control in FIGS. 7A and 7B may be used to implement a faux rotary encoder, such as the faux rotary encoder 322 of control panel 300. FIG. 7A shows a view of the faux encoder 700 and FIG. 7B shows an exploded cross-sectional view of the faux encoder 700. The faux encoder 700 includes a sealing layer 720, a capacitive touch layer 710 (e.g., a pressure sensitive p-cap layer), and a support layer 715. The support layer 715 may be rounded to impart a topography that resembles a rotary control. The capacitive touch layer 710 may be a shaped layer provided below the shaped sealing layer 720. The capacitive touch layer 710 may be a flexible layer. The sealing layer 720 may include additional topographical features 760 (e.g., transverse indentations or notches, ridges or ribs, or other surface features), which may mimic the tactile feel of a real (e.g., electro-mechanical) rotary control. It will be understood that these additional topographical features are not required for proper function of the faux encoder 700 and may be omitted. The views in FIGS. 7A and 7B are partial simplified views, in which the sealing layer 720 is shown extending over only the top surface of the other layers for illustration, however it will be understood that the sealing layer 720 may extend over the sides and completely enclose the other layers.

In operation of the faux encoder 700, a user may move or sweep their fingertip along the curved surface of the sealing layer 720, simulating the rotation of a traditional rotary encoder. However, instead of actually turning a rotary encoder, the movement of the fingertip may be detected by the capacitive touch layer 710 as a moving "footprint" of a touch along the surface of the sealing layer 720. This moving touch can then be interpreted as a degree of rotation or a distance of movement which can be passed along to a processor of the medical diagnostic machine as a user input.

As previously discussed, the order of the support layer 715 and capacitive touch layer 710 may be, such that the application of a pressure on the sealing layer 720, such as by a touch by a finger, may be detected by the capacitive touch layer 710 through the support layer 715. Additional functionality of a conventional rotary encoder, such as that of a push button, may be provided in the faux encoder 700 for example by an adjacent faux push button (not shown) or by performance of the additional function responsive to a detection of a movement different than swipe (e.g., a lift and tap, a double-tap, or other) on the faux encoder surface. A variety of other user controls may be implemented in similar manner as that of the faux encoder 700 shown in FIGS. 7A and 7B.

Figure 7C:
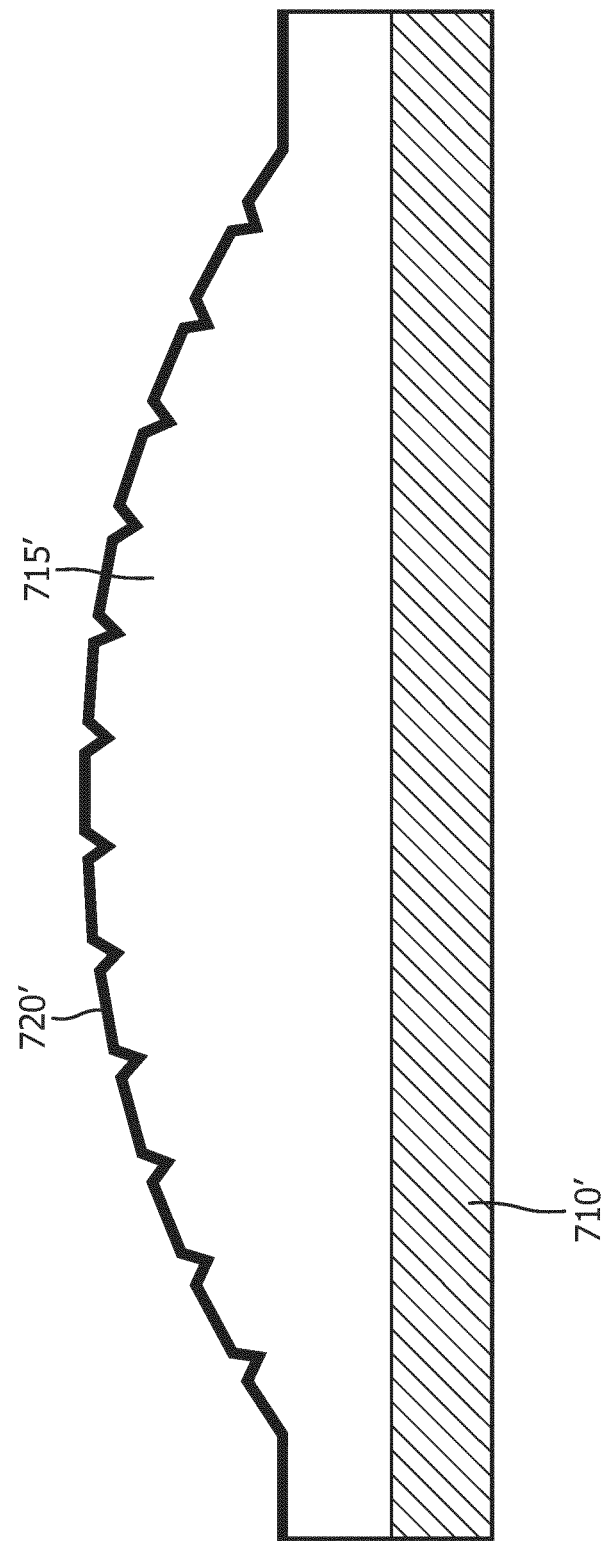
FIG. 7C shows another example of a portion of a control panel comprising a user control implemented as a faux rotary encoder.

FIG. 7C shows another example of a portion of a control panel comprising a user control implemented as a faux rotary encoder. In this example, the control panel includes a capacitive touch layer 710', a sealing layer 720', and a support layer 715'. The capacitive touch layer 710' may be a implemented using a projected capacitance sensor which is configured to be pressure-sensitive such that the capacitive touch layer 710' is operable to invoke a response (e.g., execute a command associated with the user control) when a pressure on the control panel at the location of the user control exceeds a predetermined amount. This threshold amount may be selected to correspond to a lower amount of pressure that may result from the user tactilely locating, and placing or lightly resting their finger on the control. The control panel may ignore a touch at the lower pressure and only invoke the corresponding function when the pressure exceeds the threshold, e.g., responsive to the user pressing on or otherwise operating the user control to select the corresponding function.

Returning back to FIG. 7C, in this example the capacitive touch layer 710' (e.g., p-cap layer) is a flat or generally planer layer positioned below the contoured sealing layer 720'. As described, the sealing layer 720' may be formed from a thin film of plastic which is pressure formed into the desired shape, in this case to resemble a ribbed rounded projection similar to a rotary control. A support layer 715' having a contoured upper surface with a shape corresponding to the contour of the sealing layer is provided below the sealing layer 720' to support the otherwise flexible sealing layer in its pressure formed shape. In this case the rounded shape of the faux rotary encoder may function as a topographical feature to assist the user in tactilely locating the user control. The ribbed control surface of the control panel (e.g., as may be defined by notches in the support layer and corresponding shape of the thin sealing layer) may function as secondary topographical features, which may simulate to a user the tactile feel of operating a real rotary control rather than a faux rotary control.

Figure 8:
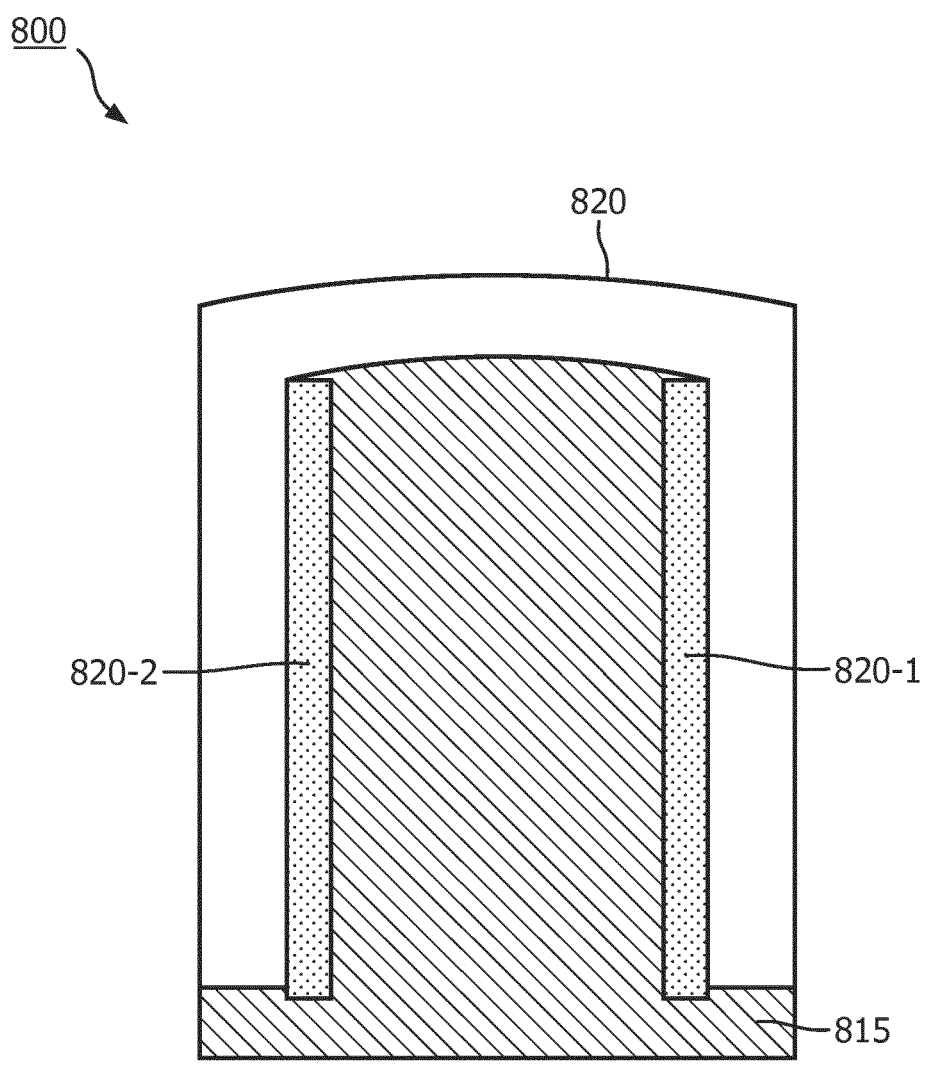
FIG. 8 is a cross-sectional illustration of an example faux slider control for a control panel in accordance with the present disclosure.

FIG. 8 is a cross-sectional view of an embodiment of a user control the form of a faux slider control which may be implemented in a control panel of the present disclosure. The faux slider control 800 may be used to implement one or more of the faux slider controls 326 of the control panel 300. A faux slider 800 may be constructed as a layered structure which includes as a cylindrical or post-shaped support layer 815. A capacitive touch layer 810 may be placed around an exterior of the support layer 815 such as along one or more sides (e.g., opposite sides) of the cylindrical support layer 815. The location of the capacitive touch layer 810 may be selected based on the expected location and/or direction of the touch. For examples, if a faux slides is designed to mimic a slider that moves side to side, capacitive touch layer 810 may be located on the opposite sides that represent the two different directions in which the slider-style control might be moved. A sealing layer 820 is provided around the capacitive touch layer 810 and support layer 815 to fully enclose the underlayers of the faux slider control 800.

In a typical operational scenario, the faux slider 800 may work by detecting pressure on opposite sides of the cylindrical shape. For instance, detecting pressure on the left side of the control shown in FIG. 8 may indicate a desire to "move" the faux slider toward the right, and detecting pressure on the right side of the control may indicate a desire to "move" the faux slider toward the left. As previously mentioned, the faux slider 800 may not actually slide or move, but is instead configured to interpret pressure applied to a side of the control as a user input corresponding to a desired movement of the control in a particular direction. In other examples, the capacitive touch layer 810 may instead be provided as a flat or generally planer layer located below the support layer 815. In such examples, the support layer and sealing layer may be configured to allow the user's finger or other portion of the user's hand (e.g., palm or side of the user's palm or finger) conductively couple to the capacitive touch layer. Additionally or optionally, a force-sensitive resistive device or a piezo-electric strain cell device may be used to allow for detecting where force is being applied to the faux control 800. For example, piezo-electric strain cells may be attached at one or more locations around the perimeter of the support layer 815 to detect strains on the support layer structure associated with applied force and the detected strains may be used to determine on which side of the structure force is being applied to and thereby the direction in which the user is operating the control. A faux slider in accordance with the present disclosure may be implemented differently, as described further below with reference to FIG. 10.

In some examples, the control panel may include a touchscreen in addition to or instead of the field control panel (e.g., control panel 304). In some examples, the user interface may include only touch screen controls on a single or multiple panels. An advantage of using a touch-sensitive, flat panel display with a programmable graphical user interface is that a single area on a control panel can serve multiple functions based on the content shown on the display. That is, programmable "soft buttons" can be made to appear on the screen in any location, can be designed to be any shape or color, and can control different functions based on the menu or page being shown. The software controlling the operator interface can determine which areas of the touch-sensitive display are dedicated to the functioning of the soft buttons and detect and interpret touches in this area as a desire to activate the corresponding function.

However existing touch-sensitive displays on medical diagnostic systems may have some shortcomings, such as the inability to locate specific controls by touch and/or the inability to rest a finger on the control once located before activating the control. The examples herein may address some of the shortcomings of existing touch-sensitive display panels.

Figure 9A:
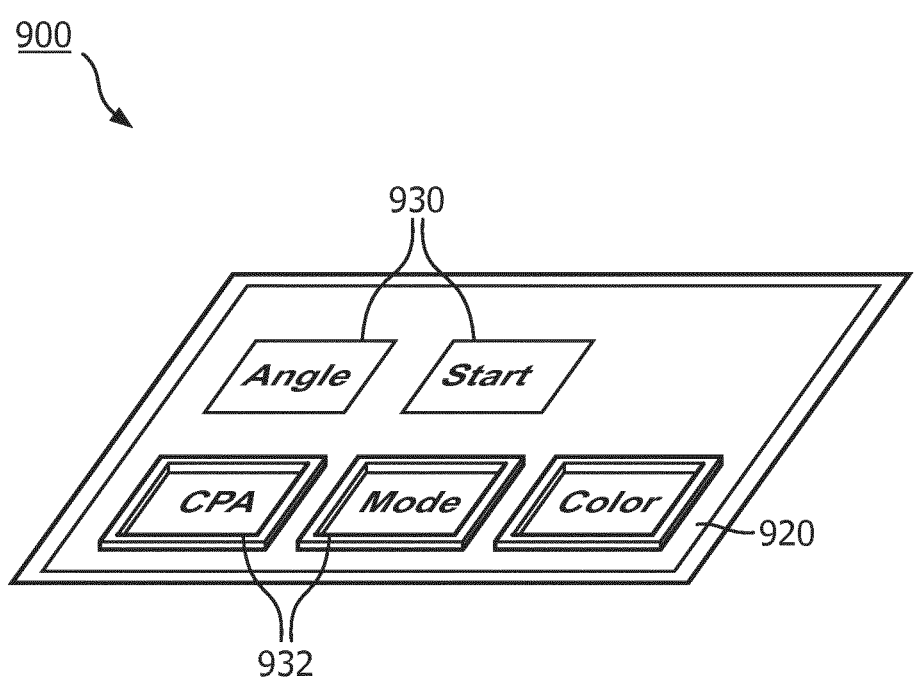
FIGS. 9A-9C are perspective, exploded and cross-sectional illustrations of a touch screen for use in a control panel in accordance with the present disclosure.
Figure 9B:
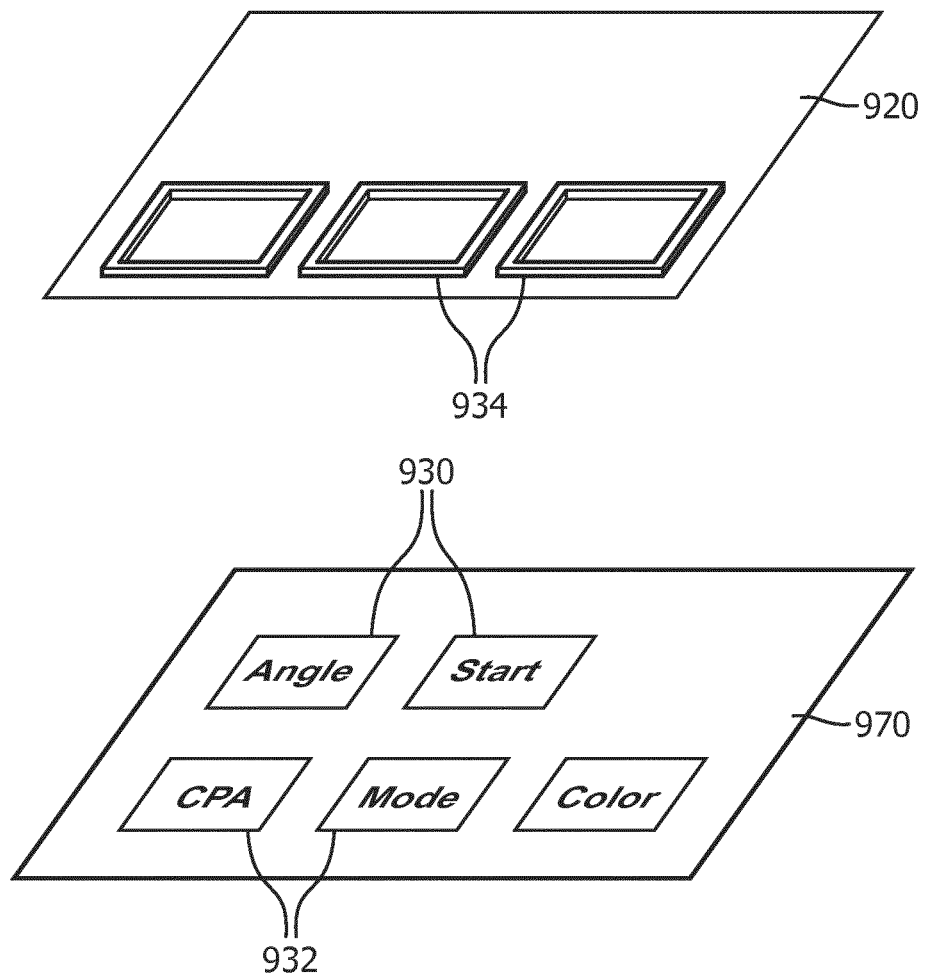
Figure 9C:
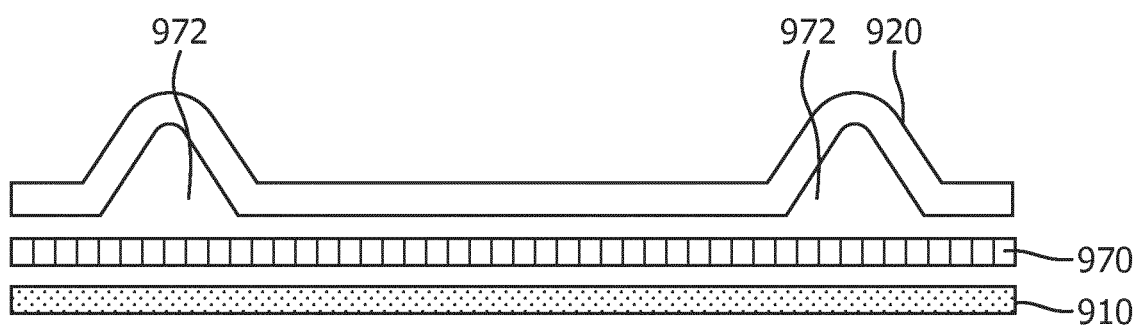

FIGS. 9A-9C show perspective, exploded and cross-sectional illustrations of a touch-sensitive, flat panel display for use in a control panel in accordance with the present disclosure. The touch-sensitive flat panel display 900 may be used to implement the display 302 of control panel 300. The display 900 may be configured to display a GUI which includes one or more soft controls. The display may be configured to provide variable-location soft controls 930 and fixed-location soft controls 932. The display may include a substantially optically transparent sealing layer 920, which may include built-in topographical features to aid an operator in locating controls by touch. Specifically, the optically transparent sealing layer 920 may include one or more topographical features 934 which may be provided at user control locations of the display that are associated with fixed-location soft controls 932.

Figure 5C:
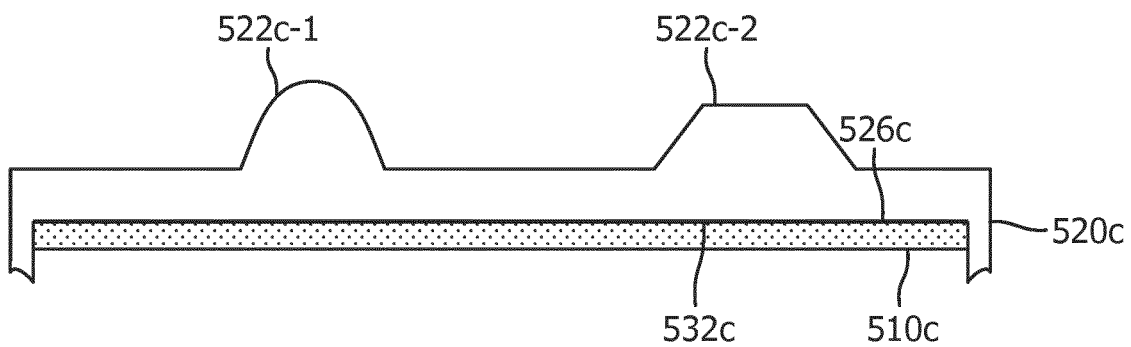

Referring to FIG. 9C, the display 900 may have a layered structure which includes a capacitive touch layer 910 and a sealing layer 920 provided as the outer-most or top layer of the display. An optically transparent cover layer 970 (e.g., glass or polycarbonate) may be placed over the capacitive touch layer 910, which similar to other examples herein may be implemented using a p-cap layer. The cover layer 970 may be a generally rigid layer that protects the underlying components of the display 900 as well as provides part of the rigid enclosure of the display 900. The capacitive touch layer 910 may be a pressure-sensitive layer which is configured to perform different functions or selectively perform a function responsive to different detected pressure on the display. The sealing layer 920 may include one or more features of other sealing layers described herein. For example, the sealing layer 920 may be a relatively thin layer (e.g., a pressure-formed film of plastic) shaped to include topographical features (e.g., features 934 in FIG. 9B) to facilitate the locating of a user control by touch. The sealing layer 920 in this example is optically transparent. The sealing layer 920 may be bonded to the cover layer 970. In this example no additional support structure is provided beyond the generally planar cover layer 970 thus when the layers are assembled, air filled gaps 972 may remain between the sealing layer 920 and the cover layer 970. An optically transparent cover layer similar to layer 970 may be optionally provided in any of the examples previously described, for example in the layered structures in FIGS. 5A and 5C, which cover layer may similarly be provided over the capacitive touch layer so as to protect the underlying capacitive touch layer.

The display 900 may be configured using known techniques to provide soft controls in any desired combination. The display may be specifically configured to provide certain controls in a fixed location (e.g., fixed-location controls 932) on the display so as to align with the location of the topographical features of the sealing layer 920. While the particular functionality of a fixed-location control 932 may change from one user interface screen to another, the location of the fixed-location control 932 may remain substantially the same, such that the user may be able to locate the fixed-location control by touch. In some examples, the topographical features 932 may be implemented as raised portions of the sealing layer 920 which may correspond to an outline of a fixed-location soft control 932, in this example raised rectangular outlines. The topographical feature need not encircle the soft control. In other examples, different arrangements may be used, for example one or more bumps, ridges or ribs, or other types of features may be provided in the sealing layer at a location corresponding a fixed-location control 932.

In a typical operational scenario, an operator may use certain variable-location buttons 930 to enter into a specific operating mode while looking at the display 900. Once entered into the proper mode, the operator may then return their focus to the patient to adjust the ultrasound probe or to the ultrasound image being displayed such as on a main display area. Then, a particular function associated with a fixed-location soft control may be performed without the operator having to look back at the flat panel display 900, as the operator may be able to located the desired control by touch such as by tactilely locating the topographical feature provided over the user control location of the desired control.

The pressure sensitive capability of the capacitive touch layer 910 of display 900, allows the user to rest a finger on the operator control located by touch without activating it until activation is desired at which time the operator may apply additional pressure to the display to activate the corresponding function.

In some examples, the transparent sealing layer 920 may extend over the entire surface of the touch screen and may be bonded to the cover layer 970 (e.g., glass or polycarbonate) of the touch screen. In other examples, the transparent sealing layer may wrap around an edge of the touch screen, and in some examples may be attached (e.g., bonded, fused, laser welded, or otherwise fastened) to a perimeter portion of a housing of the touch screen.

In any of the examples herein, user feedback to indicate the selection of a control may be provided by audible feedback such as a click sound or mechanical tactile feedback such as vibration. For example, mechanical tactile feedback may be implemented using an overall bump from a solenoid armature tapping on the back of the support layer or another part of the structure of the panel (e.g., a cover layer), a piezo-electric transducer attached to the back of the support layer or another structure, a voice-coil speaker mounted on the back of the support layer or another structure, an eccentric rotating mass vibration motor mounted on the back of the support layer or another structure, a "Force Reactor" vibration device supplied by ALPS, or any combinations thereof. The control panels herein may be configured to reduce the damping of such mechanical feedback by the support layer for example, by providing a discontinuous support layer as described herein.

Figure 10:
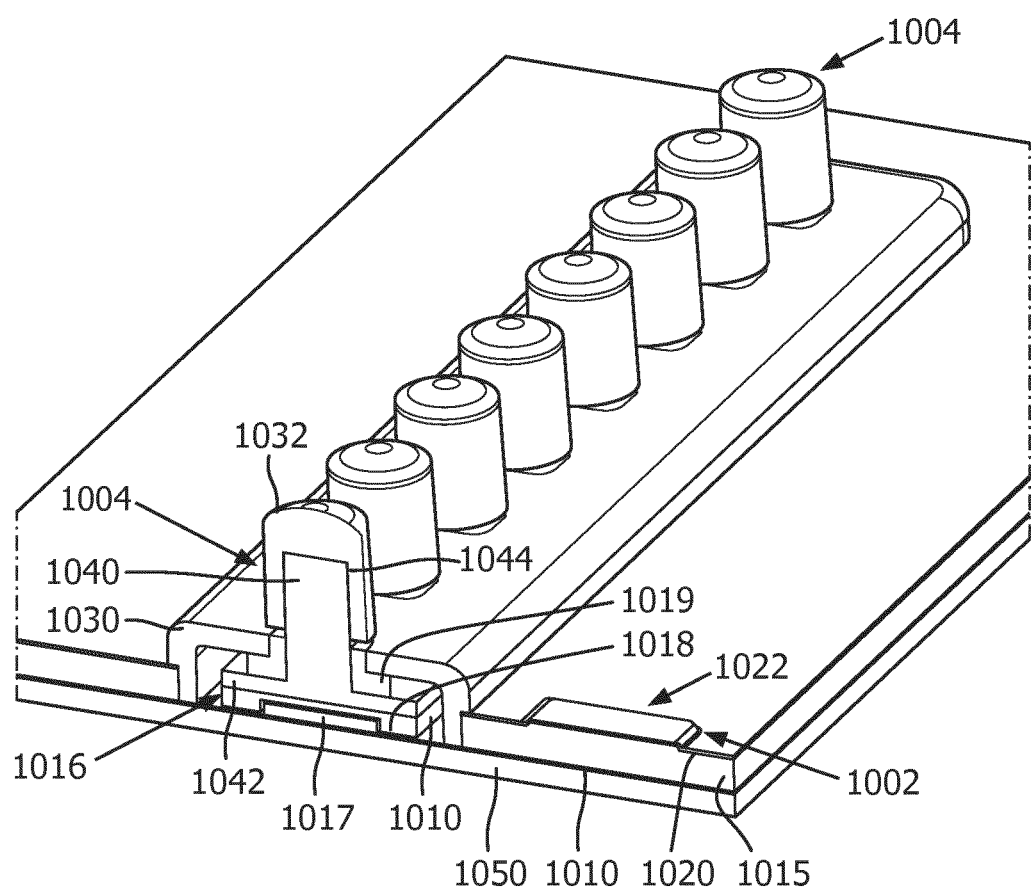
FIG. 10 shows a simplified cross-sectional view of user controls for a control panel in accordance with further examples of the present disclosure.

FIG. 10 shows a simplified cross-sectional view of user controls for a control panel in accordance with further examples of the present disclosure. The example in FIG. 10 illustrates a plurality of faux sliders 1004 and a faux button-type control 1002. The control 1002 is constructed using a pressure-sensitive capacitive layer 1010 provided below a contoured sealing layer 1020. In some examples, the capacitive layer 1010 is a flexible layer (e.g., flex circuit including conductive traces operatively arranged to provide a capacitive touch sensor) and an additional support layer (e.g., backer plate 1050) may be provided below the capacitive layer 1010. It will be understood that although a continuous capacitive layer 1010 is used for multiple ones of the user controls in this illustrated example, in other examples, individual capacitive sensors may be operatively provided at each user control area to provide the touch sensing capability for the individual user controls.

The sealing layer 1020 may be formed of a thin film of plastic, which can be transparent, partially transparent, translucent, or opaque, as may be appropriate for a particular application. The thin film, which in some examples may be 1 mm thick or less, may be shaped to include one or more topographical features, for example topographical feature 1022. A support layer 1015 fills the space between the sealing layer 1020 and the capacitive layer 1010. The support layer 1015 is relatively rigid as compared to the sealing layer 1020 and thus provides structural support for the otherwise flexible sealing layer. The sealing layer 1020 and support layer 1015 are formed of materials which do not significantly inhibit capacitive coupling between the capacitive layer 1010 and the user's finger or other portion of their hand. As noted, the sealing layer 1020 includes at least one topographical feature to aid the user in tactilely locating the one or more user controls. For example, in the case of control 1002, the topographical feature 1022 may define the shape of the button type control 1002. The sealing layer 1020 and support layer 1015 may be bonded, in some examples bonded during the forming process, with the upper surface of the support layer 1015 following the contour of the sealing layer 1020. The sealing layer 1020 may cover most or substantially the entire upper surface of a control panel.

Faux sliders 1004 may be constructed using a pressure-sensitive capacitive layer 1010 provided below a contoured sealing layer 1020. The pressure-sensitive capacitive layer 1010 may be operatively associated with a support layer or structure 1040, which may be shaped to resemble the structure of a real (electro-mechanical) slider control. In this example, the support structure 1040 includes a base 1042 and a post 1044 extending generally perpendicularly from the base 1042. The support structure 1040 may be formed of a generally rigid material, such as metal or plastic, which does not substantially inhibit capacitive coupling.

The support structure 1040 is coupled to the underlying layers via a layered structure 1016 configured to permit selectively conductively coupling the support structure 1040 to the capacitive layer 1010. In the illustrated example, the layered structure 1016 includes an electrically conductive pad 1018, which may be constructed from a conductive foam pad, and an insulating pad 1017, which may be constructed from a dielectric material such as rubber. The upper surface of the conductive pad 1018 is fixed to the bottom surface of the base 1042 and the bottom surface of the insulating pad 1017 is placed over the capacitive layer 1010 to mechanically couple the support structure 1040 to the capacitive layer 1010. The insulating pad 1017 may have a smaller footprint than the conductive pad 1018 such that the support structure 1040 is balanced over the capacitive layer 1010 and is able to see saw when force is applied to the support structure 1040, e.g., via the post 1044. For example, the insulating pad 1017 may be narrower than the conductive pad 1018 such that a gap is defined between the bottom surface of the conductive pad 1018 and the upper surface of the capacitive layer 1010. The gap prevents conductive coupling between the structure 1040 and the capacitive layer 1010 until a sufficient force is applied to the structure 1040. In the illustrated example, the conductive pad 1018 includes a recess and the insulating pad 1017 is received in the recess but extends beyond the depth of the recess. In this example, a portion of the conductive pad 1018 extends over the insulating pad 1017 between the insulating pad 1017 and the base 1042 thereby providing a larger conductive contact area between the pad 1018 and base 1042. In other examples, the insulating pad 1017 may be provided in a through slot in the conductive pad 1018 and may contact the base 1042 of support structure 1040.

During normal use, upon the application of force in one direction, one side of the base 1042 conductively couples to the capacitive layer 1010 via the conductive pad 1018. Similarly upon application of force in the opposite direction, the opposite side of the base 1042 conductively couples to the capacitive layer 1010 via the conductive pad 1018. When no force is applied, the structure 1040 returns to its nominal or non-deflected position e.g., with the post 1044 extending generally perpendicularly relative to the capacitive layer 1010. The structure 1040 is substantially fully enclosed below a sealing layer. In the illustrated examples, the structure 1040 is enclosed by a sealing cap 1032 provided over a portion of the post 1044 and a shoulder 1030 substantially enclosing the base 1042 and layered structure 1016. The sealing cap 1032 is made from a material which permits conductive coupling between the user's hand and the capacitive layer 1010. Optionally, the shoulder 1030 may made from a material which permits conductive coupling between the user's hand and the capacitive layer 1010. In such examples, an insulating gasket 1019 may be provided around the post 1044 to electrically insulate the post 1044 from a conductive shoulder 1030. Although the cap 1032 and shoulder 1030 are illustrated as separate sealing components, in some examples, the cap 1032 and shoulder 1030 may be implemented using an integral or continuous layer, which may also be integral or continuous with the sealing layer 1020. In some examples, the shoulder, the cap, and the sealing layer, or any combination thereof may be made from the same material.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this invention may be apparent to those skilled in the art upon studying the disclosure, or may be experienced by persons employing the novel system and method of the present invention. Another advantage of the present systems and method may be that conventional medical image systems can be easily upgraded to incorporate the features and advantages of the present systems, devices, and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound system, comprising
an ultrasound probe configured to control transmission of ultrasound and reception of ultrasound echoes with the probe; and
a control panel comprising:
a control surface comprising a plurality of user control areas arranged at fixed locations along the control surface;
a pressure-sensitive capacitive touch layer; and
a sealing layer disposed over the capacitive touch layer and extending continuously over the plurality of user control areas, the sealing layer comprising at least one topographical feature associated with at least one user control area of the plurality of user control areas;
wherein the at least one topographic feature is arranged at a location corresponding to an active portion of the pressure-sensitive, capacitive-touch layer, and wherein the active portion is configured to detect an amount of pressure associated with a touch applied to the control surface at the at least one user control area and invoke a user control function associated with the at least one user control area responsive to the touch only if the amount of detected pressure exceeds a threshold amount,
wherein the at least one topographic feature comprises a cylindrical shape to form a faux slider, wherein the pressure-sensitive capacitive touch layer is configured to detect the touch applied to opposing sides of the cylindrical shape, wherein a value is increased responsive to the touch applied to a first side of the opposing sides and the value is decreased responsive to the touch applied to a second side of the opposing sides.

2. The ultrasound system of claim 1, further comprising at least one more topographical feature shaped to resemble a mechanical control selected from the group consisting of pushbutton, switch, lever, knob, trackpad, and rotary encoder.

3. The ultrasound system of claim 1, wherein the pressure-sensitive capacitive touch layer is a layer spanning the plurality of user control areas.

4. The ultrasound system of claim 1, further comprising a support layer below the pressure-sensitive capacitive touch layer.

5. The ultrasound system of claim 1, further comprising a support layer between the pressure-sensitive capacitive touch layer and the sealing layer, wherein an upper surface of the support layer is shaped to correspond to a contour of the sealing layer and the pressure-sensitive capacitive touch layer.

6. The ultrasound system of claim 1, wherein the pressure-sensitive capacitive touch layer is incorporated into a touch sensitive display, and wherein the sealing layer is optically transparent.

7. The ultrasound system of claim 1, further comprising a glass or transparent plastic layer between the pressure-sensitive capacitive touch layer and the sealing layer.

8. The ultrasound system of claim 1, wherein the sealing layer comprises a sheet of polymer.

9. The ultrasound system of claim 8, wherein the sealing layer comprises a sheet of polyethylene terephthalate (PET).

10. The ultrasound system of claim 1, wherein the faux slider control is configured to initiate an increase or a decrease of time gain compensation (TGC) of an ultrasound image responsive to the touch.

11. The ultrasound system of claim 10, wherein the faux slider control is configured to center the TGC of the ultrasound image responsive to the touch on top or simultaneously on both sides.

12. The ultrasound system of claim 1, further comprising at least one more topographic feature comprising a rotary encoder.

13. The ultrasound system of claim 12, wherein the rotary encoder is configured to modify a user feature in a rotation in response to a user touch.

14. The ultrasound system of claim 1, further comprising:
a support structure disposed at a location of the faux slider, wherein the support structure comprises a base and a post extending perpendicularly from the base; and
a layered structure comprising an electrically conductive pad and an insulating pad, wherein an upper surface of the electrically conductive pad is coupled to a bottom surface of the base and a bottom surface of the insulating pad is coupled to the capacitive touch layer.

15. The ultrasound system of claim 14, wherein the insulating pad has a smaller footprint than the conductive pad.

16. The ultrasound system of claim 15, wherein the conductive pad is configured to couple to the capacitive touch layer when the pressure associated with the touch applied to the first side or the second side exceeds the threshold amount.

* * * * *